US00PP15243P2

(12) United States Plant Patent
Rusow

(10) Patent No.: US PP15,243 P2
(45) Date of Patent: Oct. 19, 2004

(54) *BUXUS* PLANT NAMED 'MONRUE'

(50) Latin Name: *Buxus sempervirens*
Varietal Denomination: Monrue

(75) Inventor: Greg Rusow, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 10/724,994

(22) Filed: Dec. 1, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct *Buxus* plant named 'Monrue', characterized by its upright and columnar plant habit; vigorous growth habit; freely branching habit and short internodes; dense and bushy plant form; dark green foliage color that is retained throughout the year; and relative resistance to root rot pathogens common to *Buxus*.

1 Drawing Sheet

Botanical classification/cultivar designation: *Buxus sempervirens* cultivar Monrue.

BACKGROUND OF THE INVENTION

The present invention relates to a new and distinct cultivar of *Buxus*, botanically known as *Buxus sempervirens,* commercially known as Boxwood, and hereinafter referred to by the name 'Monrue'.

The new *Buxus* is a naturally-occurring whole plant mutation of the *Buxus sempervirens* cultivar Graham Blandy, not patented. The new *Buxus* was discovered and selected by the Inventor in a controlled environment in Dayton, Oreg. in June, 1995, as a single plant within a population of plants of the cultivar Graham Blandy.

Asexual reproduction of the new *Buxus* by cuttings taken in a controlled environment in Dayton, Oreg., since the fall of 1998, has shown that the unique features of this new *Buxus* are stable and reproduced true to type in successive generations.

SUMMARY OF THE INVENTION

The cultivar Monrue has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Monrue'. These characteristics in combination distinguish 'Monrue' as a new and distinct cultivar of *Buxus:*

1. Upright and columnar plant habit.
2. Vigorous growth habit.
3. Freely branching habit and short internodes, dense and bushy plant form.
4. Dark green foliage color that is retained throughout the year.
5. Relatively resistant to root rot pathogens common to *Buxus.*

Plants of the new *Buxus* differ from plants of the parent, the cultivar Graham Blandy, in leaf coloration as plants of the cultivar Graham Blandy do not retain their green coloration during the winter. In addition, plants of the cultivar Graham Blandy are not as resistant to root rot pathogens, such as *Phytophthora*, than plants of the cultivar Monrue.

Plants of the new *Buxus* can be compared to plants of the *Buxus* cultivar Handsworthii, not patented. In side-by-side comparisons conducted in Dayton, Oreg., plants of the new *Buxus* differed from plants of the cultivar Handsworthii in the following characteristics:

1. Plants of the new *Buxus* had shorter internodes and were denser and bushier than plants of the cultivar Handsworthii.
2. Lateral branches of plants of the new *Buxus* were more flexible and not as upright as lateral branches of plants of the cultivar Handsworthii.
3. Plants of the new *Buxus* had flatter and thinner leaves than plants of the cultivar Handsworthii.
4. Plants of the new *Buxus* had lighter green-colored fully expanded foliage than plants of the cultivar Handsworthii.

BRIEF DESCRIPTION OF THE PHOTOGRAPHS

The accompanying colored photographs illustrate the overall appearance of the new *Buxus*, showing the colors as true as it is reasonably possible to obtain in colored reproductions of this type. Colors in the photographs may differ slightly from the color values cited in the detailed botanical description which accurately describe the colors of the new *Buxus.*

The photograph at the top of the sheet comprises a close-up view of typical leaves of 'Monrue'.

The photograph at the bottom of the sheet is a side perspective view of a typical plant of 'Monrue' grown in a container.

DETAILED BOTANICAL DESCRIPTION

The aforementioned photographs and following observations and measurements describe plants grown in Azusa, Calif., grown in five-gallon containers in an outdoor nursery during the summer and under conditions which closely approximate commercial production. During the production of the plants, day temperatures ranged from 29 to 32° C. and night temperatures ranged from 13 to 16° C. Plants were about five years old when the photographs and the description were taken. Plants were pruned to maintain the plant's symmetry. In the description color references are made to The Royal Horticultural Society Colour Chart, 1995 Edition, except where general terms of ordinary dictionary significance are used.

Botanical classification: *Buxus sempervirens* cultivar Monrue.

Parentage: Naturally-occurring whole plant mutation of the *Buxus sempervirens* cultivar Graham Blandy, not patented.

Propagation:

*Type.*—By cuttings.

*Time to initiate roots.*—About 90 days at 13° C.

*Time to produce a rooted young plant.*—About 270 days at 13° C.

*Root description.*—Thick, whitish in color.

*Rooting habit.*—Moderately dense; freely branching.

Plant description:

*Plant type.*—Perennial evergreen shrub.

*Plant form and growth habit.*—Upright and columnar plant habit. Vigorous growth habit. Short internodes, dense and bushy form.

*Branching habit.*—Freely branching; usually about five main branches each with about 15 to 18 lateral branches.

*Plant height.*—About 80 cm.

*Plant diameter* (*area of spread*).—About 38 cm.

*Lateral branch description.*—Length, primary branches: About 70 cm. Length, lateral branches: About 20 cm. Diameter, primary branches: About 2 cm. Diameter, lateral branches: About 4 mm. Internode length: About 1.5 cm. Aspect: Upright. Texture: Young stems, slightly pubescent; woody stems, rough. Color: Young stems: 144A. Woody stems: 195A.

*Foliage description.*—Arrangement: Opposite, simple. Length: About 2 to 3 cm. Width: About 1.2 to 1.7 cm. Shape: Ovate. Apex: Slightly emarginate. Base: Attenuate. Margin: Entire. Texture, upper and lower surfaces: Smooth, glabrous; leathery. Venation pattern: Pinnate. Color: Developing leaves, upper and lower surfaces: 144A. Fully expanded leaves, upper surface: Darker than 147A. Fully expanded leaves, lower surface: 147B. Venation, upper surface: 147A. Venation, lower surface: 147C. Petiole: Length: About 3 mm. Diameter: About 1 mm. Texture, upper and lower surfaces: Smooth, glabrous. Color, upper and lower surfaces: 146B.

Flower description: Flower development has not been observed on plants of the new *Buxus*.

Disease/pest resistance: Plants of the new *Buxus* have been observed to be relatively resistant to root rot pathogens, such as *Phytophthora*. Plants of the new *Buxus* have not been observed to be resistant to other pathogens and pests common to *Buxus*.

Garden performance: Plants of the new *Buxus* have been observed to have excellent tolerance to wind, rain and temperatures from −6° C. to 43° C.

It is claimed:

1. A new and distinct *Buxus* plant named 'Monrue', as illustrated and described.

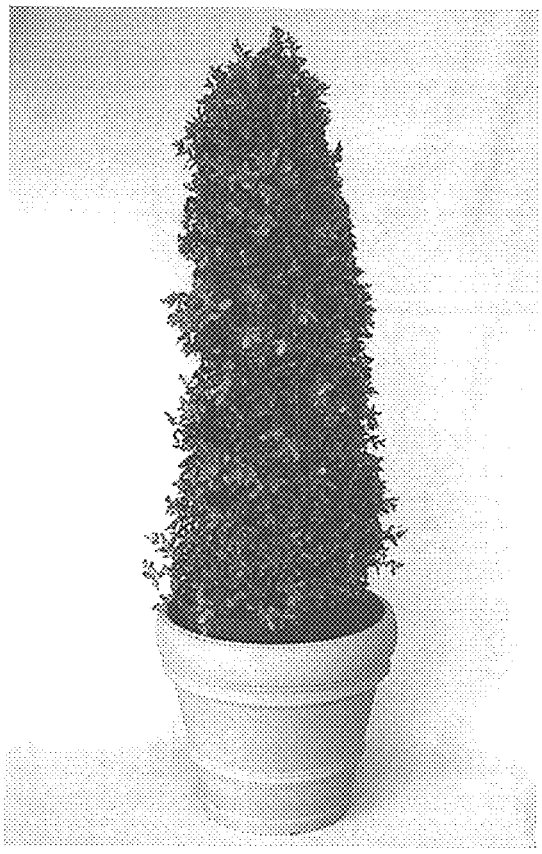
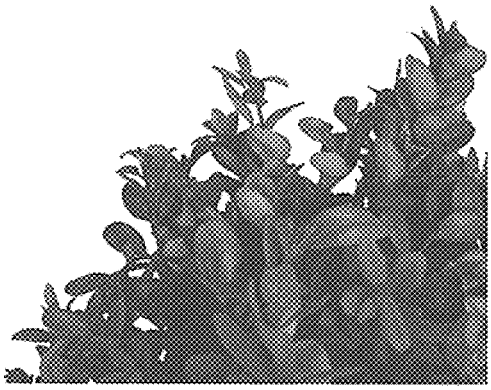

* * * * *